United States Patent [19]

Brown et al.

[11] Patent Number: 4,694,008
[45] Date of Patent: Sep. 15, 1987

[54] CHEMICAL COMPOUNDS

[75] Inventors: Thomas H. Brown, Tewin; Graham J. Durant, Welwyn, both of England

[73] Assignee: Smith Kline & French Laboratories Limited, Welwyn Garden City, England

[21] Appl. No.: 765,766

[22] Filed: Aug. 15, 1985

[30] Foreign Application Priority Data

Aug. 23, 1984 [GB] United Kingdom ................. 8421427

[51] Int. Cl.$^4$ ................... A61K 31/505; C07D 239/24
[52] U.S. Cl. .................................... 514/269; 514/272; 544/319; 544/320; 540/450; 540/524
[58] Field of Search ................ 544/319, 320; 514/269, 514/272

[56] References Cited

U.S. PATENT DOCUMENTS

| | | | |
|---|---|---|---|
| 4,145,546 | 3/1979 | Brown et al. | 544/310 |
| 4,227,000 | 10/1980 | Brown | 544/321 |
| 4,234,588 | 11/1980 | Brown et al. | 544/320 |
| 4,255,428 | 3/1981 | Brown | 544/320 |
| 4,385,058 | 5/1983 | Cooper et al. | 544/320 |
| 4,463,005 | 7/1984 | Jones et al. | 514/269 |
| 4,496,567 | 1/1985 | Brown et al. | 544/321 |
| 4,521,418 | 6/1985 | Brown et al. | 544/320 |
| 4,523,015 | 6/1985 | Brown | 544/320 |
| 4,524,071 | 6/1985 | Price et al. | 544/320 |
| 4,539,207 | 9/1985 | Brown et al. | 544/320 |
| 4,540,699 | 9/1985 | Brown et al. | 544/320 |

FOREIGN PATENT DOCUMENTS

| | | |
|---|---|---|
| 10894 | 5/1980 | European Pat. Off. . |
| 60697 | 9/1982 | European Pat. Off. . |
| 83186A | 7/1983 | European Pat. Off. . |
| 55-115860 | 9/1980 | Japan . |
| 55-115877 | 9/1980 | Japan . |

Primary Examiner—Donald G. Daus
Assistant Examiner—Barbara Cassatt
Attorney, Agent, or Firm—Linda E. Hall; Stuart R. Suter; Alan D. Lourie

[57] ABSTRACT

This invention relates to 5-oxypyrimidinone compounds having $H_2$-antagonist activity. A particular compound of the invention is 2-[3-(3-piperidinomethyl)-phenoxy)propyl]-5-benzyloxypyrimidin-4-one.

10 Claims, No Drawings

CHEMICAL COMPOUNDS

This invention relates to 5-oxypyrimidinone derivatives, pharmaceutical compositions containing them, and a method of blocking histamine $H_2$-receptors by administering them.

Histamine, a physiologically active compound endogenous in mammals, exerts its action by interacting with certain sites called receptors. One type of receptor is known as a histamine $H_1$-receptor (Ash and Schild, Brit. J. Pharmac. Chemother. 27 427 (1966)) and the actions of histamine mediated through these receptors are blocked by drugs commonly called "antihistamines" (histamine $H_1$-antagonists) a common example of which is mepyramine. A second type of histamine receptor is known as the $H_2$-receptor (Black et al. Nature 1972, 236, 385). These receptors are not blocked by mepyramine but are blocked by burimamide. Compounds which block these histamine $H_2$-receptors are called histamine $H_2$-antagonists.

Histamine $H_2$-antagonists are useful in treating disease conditions caused by the biological effects of histamine mediated through $H_2$-receptors, for example, as inhibitors of gastric acid secretion, in the treatment of inflammation mediated through histamine $H_2$-receptors and as agents which act on the cardiovascular system, for example, as inhibitors of effects of histamine on blood pressure mediated through histamine $H_2$-receptors.

Cimetidine is an example of a histamine $H_2$-antagonist. Cimetidine has been shown to be useful in the treatment of duodenal, gastric, recurrent and stomal ulceration, and reflux oesophagitis and in the management of patients who are at high risk from haemorrhage of the upper gastrointestinal tract.

In some physiological conditions the biological actions of histamine are mediated through both histamine $H_1$- and $H_2$-receptors and blockade of both types of receptors is useful. These conditions include inflammation mediated by histamine, for example skin inflammation, and those hypersensitivity responses due to the action of histamine at $H_1$- and $H_2$-receptors, for example allergies.

A small group of compounds has now been invented, which compounds have a 5-oxy substituent on a pyrimidin-4-one ring and have a particularly favourable level of activity as $H_2$-antagonists.

Accordingly the present invention provides a compound of the formula (I) :

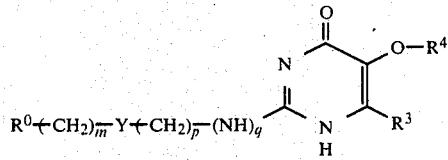

or a salt thereof, wherein:

$R^o$ is 2-guanidinothiazol-4-yl or a group $R^1R^2N(CH_2)_n$—Z wherein:

$R^1$ and $R^2$ are independently hydrogen, $C_{1-6}$alkyl, phenyl($C_{1-6}$)alkyl, furanyl($C_{1-6}$)alkyl, thienyl($C_{1-6}$)alkyl, $C_{3-10}$ cycloalkyl, hydroxy($C_{2-6}$)alkyl, or halo($C_{2-6}$)alkyl (wherein said hydroxy and halo groups are not substituted on the carbon atom adjacent to the nitrogen atom); or $R^1$ and $R^2$ together represent —$(CH_2)_r$— wherein r is 4 to 7, to form together with the nitrogen atom to which they are attached a 5–8 membered saturated ring;

n is an integer from 1 to 6;

Z is 2,5-furanyl, 2,5-thienyl, 2,4-pyridyl wherein the $R^1R^2N(CH_2)_n$ group is in the 4-position, 2,4-thiazolyl wherein the $R^1R^2N(CH_2)_n$ group is in the 2-position, or 1,3- or 1,4-phenylene;

m is one; or if Z is pyridyl or phenylene m may also be zero;

Y is oxygen, sulphur or methylene; or if Z is furanyl, thienyl or thiazolyl Y may also be a bond;

p is two, three or four;

q is zero or one;

$R^3$ is hydrogen or $C_{1-6}$alkyl; and $R^4$ is hydrogen, optionally substituted $C_{1-6}$alkyl, $C_{3-10}$cycloalkyl, $C_{3-10}$cycloalkyl($C_{1-6}$) alkyl, $C_{2-6}$alkenyl or $C_{2-6}$alkynyl, and when q is zero $R^4$ may also be —$(CH_2)_s$—B wherein s is 1 to 6 and B is optionally substituted aryl or heteroaryl.

The compounds of this invention are preferably provided in a form suitable for pharmaceutical use as a compound of the formula (I) or a pharmaceutically acceptable salt thereof.

When used herein 'alkyl' means groups that are either straight-chained or branched. In general preferred alkyl groups are methyl and ethyl.

Suitably $R^1$ is phenyl($C_{1-6}$)alkyl for example benzyl or phenethyl, furanyl($C_{1-6}$)alkyl such as furanylmethyl or thienyl($C_{1-6}$)alkyl such as thienylmethyl, halo($C_{2-6}$)alkyl for example 2,2,2-trifluoroethyl, or $C_{3-10}$cycloalkyl for example cyclohexyl. More suitably $R^1$ is $C_{1-6}$alkyl, for example methyl, ethyl or propyl.

Suitably $R^2$ is hydrogen or $C_{1-6}$alkyl, for example methyl, ethyl or propyl.

Suitable $R^1$ and $R^2$ have the same value, for example they both are methyl or they are both ethyl. In another suitable aspect $R^1$ and $R^2$ together with the nitrogen atom to which they are attached form a pyrrolidino, piperidino or hexahydroazepino ring, preferably a piperidino ring.

Preferably n is one.

Suitably Z is 2,5-furanyl or 2,5-thienyl. In such compounds preferably Y is sulphur. For example $R^1R^2N(CH_2)_n$—Z—$(CH_2)_m$—Y may represent 5-dimethylaminomethylfuran-2-ylmethylthio, 5-piperidinomethylfuran-2-ylmethylthio or 5-pyrrolidinomethylfuran-2-ylmethylthio.

In another aspect Z is 2,4-thiazolyl. In such compounds preferably Y is sulphur, for example $R^1R^2N(CH_2)_n$—Z—$(CH_2)_m$—Y—may represent 2-dimethylaminomethylthiazol-4-ylmethylthio. In a further aspect $R^o$ is 2-guanidinothiazol-4-yl, in such compounds preferably Y is sulphur, for example $R^o$—$(CH_2)_m$—Y—may represent 2-guanidinothiazol4-methylthio.

In a preferred aspect Z is 2,4-pyridyl. In an alternative preferred aspect Z is 1,3-phenylene. In each type of compound preferably —$(CH_2)_m$Y—$(CH_2)_p$—is —O—$(CH_2)_3$—or —$CH_2SCH_2CH_2$—. For example $R^1R^2N(CH_2)_n$—Z—$(CH_2)_m$—Y—$(CH_2)_p$—may represent:

4-dimethylaminomethylpyrid-2-ylmethylthioethyl,
4-piperidinomethylpyrid-2-ylmethylthioethyl,
4-dimethylaminomethylpyrid-2-yloxypropyl,
4-piperidinomethylpyrid-2-yloxypropyl,
3-dimethylaminomethylphenoxypropyl,
3-piperidinomethylphenoxypropyl,
3-dimethylaminomethylphenylmethylthioethyl, 3-piperidinomethylphenylmethylthioethyl or 3-pyrrolidinomethylphenoxypropyl.

pyrimidinone ring, when q is one, may also exist in the following tautomeric forms :

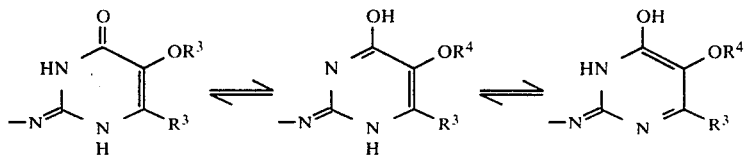

Preferably p is 3 when m is zero. Preferably p is 2 when m is one.

Suitably q is zero. Suitably q is one.

Suitably $R^3$ is $C_{1-6}$alkyl for example methyl. Preferably $R^3$ is hydrogen.

$R^4$ is suitably $C_{3-10}$cycloalkyl, for example cyclopentyl or cyclohexyl; $C_{3-10}$cycloalkyl($C_{1-6}$)alkyl for example cyclobutylmethyl, cyclopentylmethyl or cyclohexylmethyl; $C_{2-6}$alkenyl for example allyl; $C_{2-6}$alkynyl for example propargyl; or when $R^4$ is substituted $C_{1-6}$alkyl it is substituted on other than the carbon atom adjacent to the oxygen atom, and suitable substituents for $R^4$ being $C_{1-6}$alkyl include amino, di-($C_{1-6}$)alkylamino, hydroxy, $C_{1-6}$alkoxy and $C_{1-6}$alkanoyloxy.

Favourably $R^4$ is hydrogen. Preferably $R^4$ is $C_{1-6}$alkyl for example methyl, ethyl, n-propyl, isopropyl or n-butyl. Of these methyl is favoured.

When q is zero, suitably s is 1 or 2, preferably s is 1. Suitably B is aryl such as phenyl, -(1,3-benzodioxolyl) or naphthyl. Suitably B is heteroaryl such as pyridyl, N-oxopyridyl, furyl, thienyl, thiazolyl, quinolyl, isoquinolyl, benzimidazolyl, benzthiazolyl, 5,6,7,8-tetrahydroquinolyl, pyridazinyl, pyrazinyl, imidazolyl, pyrimidinyl, isothiazolyl, thiadiazolyl or oxazolyl.

When B is substituted aryl or heteroaryl suitable substituents include $C_{1-4}$alkyl, $C_{1-4}$alkoxy, halo, hydroxy and amino. Examples of B, when substituted phenyl, include $C_{1-4}$alkoxyphenyl, in particular 3-methoxyphenyl, 4-methoxyphenyl or 3,4-dimethoxyphenyl. Examples of B, when optionally substituted heteroaryl, include 2-furyl, 2-thienyl, 2-pyridyl, 3-pyridyl, 4-pyridyl, 2-thiazolyl, 2-imidazolyl, 2-pyrimidinyl, 2-pyrazinyl, 3-pyridazinyl, 3-quinolyl or 1-isoquinolyl groups which groups are optionally substituted by one or more $C_{1-4}$alkyl or $C_{1-4}$alkoxy groups, or a pyridyl or pyrimidinyl group substituted by hydroxy, and especially 3-pyridyl, 6-methyl-3-pyridyl, 5,6-dimethyl-3-pyridyl, 6-methoxy-3-pyridyl, 2-methoxy-4-pyridyl, 6-hydroxy3-pyridyl and 2-hydroxy-4-pyridyl.

In another aspect compounds of the formula (I) wherein B is phenyl, pyridyl, furyl or thienyl can be substituted by a group $R^aR^bN(CH_2)_t$- wherein $R^a$ and $R^b$ are as defined hereinbefore for $R^1$ and $R^2$ and and Rb are as defined hereinbefore for $R^1$ and $R^2$ and t is 1 to 6. Suitably Ra and Rb are both methyl and t is 1.

Preferably when q is zero, $R^4$ is benzyl.

In a favoured aspect the present invention provides compounds of the formula (I) wherein $R^1R^2N(CH_2)_n$—is dimethylaminomethyl or piperidinomethyl, Z is 1,3-phenylene, m is zero, Y is oxygen, p is 3, q is zero or one, and $R^3$ is hydrogen.

The compounds of the formula (I), are shown and described as 4-pyrimidinone derivatives and these derivatives exist in equilibrium with the corresponding -pyrimidinone tautomers. These compounds also exist to a lesser extent as the hydroxy tautomers and the The activity of the compounds of formula (I) as histamine $H_2$-antagonists can be demonstrated by their ability to inhibit histamine-stimulated secretion of gastric acid from the lumen-perfused stomachs of rats anaesthetised with urethane, and to reverse histamineinduced inhibition of contractions of the isolated rat uterus. These are actions of histamine which, according to Ash and Schild, Brit. J. Pharmac. Chemother. 27 247 (1966), are not mediated by histamine $H_1$-receptors.

The histamine $H_2$-antagonist activity of the compounds can also be demonstrated by the inhibition of histamine-stimulated acid secretion in the Heidenhain Pouch Dog, the inhibition of histamine-induced tachycardia in the isolated guinea pig right atrium and the inhibition of histamine-induced vasodilatation in the anaesthetised cat.

The measurement of inhibition of histamine-stimulated secretion of gastric acid from the lumen-perfused stomachs of rats anaesthetised with urethane, and the measurement of inhibition of histamine-induced tachycardia in the isolated guinea pig right atrium, are detailed in U.S. Pat. No. 4,385,058.

To illustrate the level of activity of the compounds of the invention we have determined that the products of Examples 1 and 5 have $ED_{50}$ values in the lumen-perfused rat test of less than 0.1 micromol kg$^{-}$i.v. and $pA_2$ values in the guinea pig atrium test of more than seven.

In order to use the compounds of the formula (I) or pharmaceutically acceptable salts thereof for medical purposes, they are normally formulated in accordance with standard pharmaceutical practice as pharmaceutical compositions.

The invention further provides pharmaceutical compositions comprising a compound of the formula (I) or a pharmaceutically acceptable salt thereof and a pharmaceutically acceptable carrier.

The compounds of the formula (I) and their pharmaceutically acceptable salts may be administered, for example, orally, parenterally, cutaneously or rectally.

The compounds of the formula (I) and their pharmaceutically acceptable salts which are active when given orally can be formulated as syrups, tablets, capsules and lozenges. A syrup formulation will generally consist of a suspension or solution of the compound or pharmaceutically acceptable salt in a suitable liquid carrier for example, ethanol, glycerine or water with a flavouring or colouring agent. Where the composition is in the form of a tablet, any suitable pharmaceutical carrier routinely used for preparing solid formulations may be used. Examples of such carriers include magnesium stearate, starch, lactose, sucrose and cellulose.

Typical parenteral compositions consist of a solution or suspension of the compound or pharmaceutically acceptable salt in a sterile aqueous carrier or parenterally acceptable oil.

Typical compositions for administration to the skin include lotions and creams in which the compound of the formula (I) or pharmaceutically acceptable salt thereof is contained in a liquid vehicle.

A typical suppository formulation comprises a compound of formula (I) or a pharmaceutically acceptable salt thereof which is active when administered in this way, with a binding and/or lubricating agent such as gelatin or cocoa butter or other low melting vegetable waxes or fats.

Preferably the composition is in unit dose form such as a tablet or capsule.

Each dosage unit for oral administration contains preferably from 15 to 250 mg (and for parenteral administration contains preferably from 0.5 to 25 mg) of a compound of the formula (I) or a pharmaceutically acceptable salt thereof calculated as the free base.

The invention also provides a method of blocking histamine $H_2$-receptors which comprises administering to an animal an effective amount to block said receptors of a compound of the formula (I) or a pharmaceutically acceptable salt thereof.

The pharmaceutically acceptable compounds of the invention will normally be administered to a subject for the treatment of peptic ulcers and other conditions caused or exacerbated by gastric acidity in the same general manner as that employed for known histamine $H_2$-antagonists, due allowance being made in terms of dose levels for the potency of the compound of the present invention relative to known histamine $H_2$-antagonists. The daily dosage regimen for example for an adult patient may be an oral dose of between 15 mg and 1000 mg, preferably between 20 mg and 250 mg, or an intravenous, subcutaneous, or intramuscular dose of between 0.5 mg and 100 mg, preferably between 1 mg and 20 mg, of the compound of the formula (I) or a pharmaceutically acceptable salt thereof calculated as the free base, the compound being administered 1 to 4 times per day.

The compounds of the formula (I) and salts thereof may be prepared by a process which comprises :

(a) ror compounds of the formula (I) and salts thereof one, reacting a compound of the formula (II) with a compound of the formula (III) :

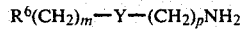

(II)

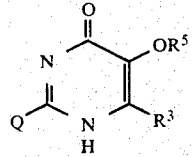

(III)

wherein m, Y, p and $R^3$ are as hereinbefore defined, $R^6$ is a group $R^o$ as hereinbefore defined or $R^6$ is a furan-2-yl or thien-2-yl group; $R^5$ is an optionally protected group $R^4$ with the proviso that it is not hydrogen (wherein $R^4$ is as hereinbefore defined); and Q is a group displaceable by an amine; or (b) for compounds of the formula (I) wherein m is one and Y is sulphur, reacting a compound of the formula (IV) with a compound of the formula (V) :

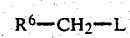

(IV)

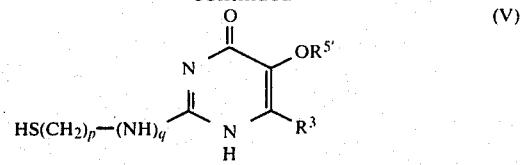

(V)

wherein $R^6$, p, q and $R^3$ are as hereinbefore defined, $R^{5'}$ is an optionally protected group $R^4$, and L is a moiety displaceable by thiol or chemical equivalent thereof; or (c) for compounds of the formula (I) wherein m is one and Y is sulphur, reacting a compound of the formula (VI) or chemical equivalent thereof with a compound of the formula (VII):

$$R^6CH_2SH \qquad (VI)$$

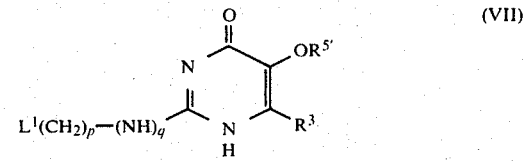

(VII)

wherein $R^6$, p, q, $R^{5'}$ and $R^3$ are as hereinbefore defined and $L^l$ is a moiety displaceable by thiol or chemical equivalent thereof; or (d) reacting a compound of the formula (VIII) with a compound of the formula (IX) or chemical equivalent thereof:

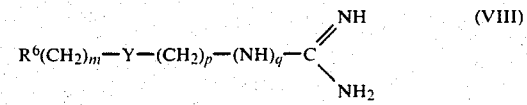

(VIII)

(IX)

wherein $R^6$, m, Y, p, q, $R^3$ and $R^5$ are as hereinbefore defined, and $R^7$ is an ester-forming group; or (e) for compounds of the formula (I) wherein Z is 2,4-pyridyl, m is zero and Y is oxygen, reacting a compound of the formula (X) with a compound of the formula (XI) or derivative thereof that permits reaction to occur:

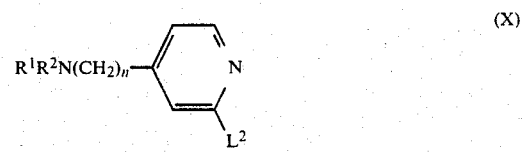

(X)

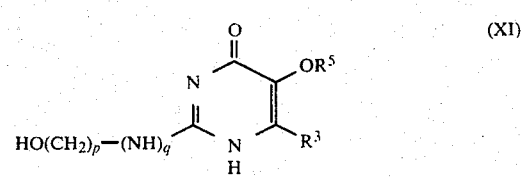

(XI)

wherein $R^1$, $R^2$, n, p, q, $R^3$ and $R^5$ are as hereinbefore defined and L is a group displaceable by hydroxy or the equivalent thereof; or (f) for compounds of the formula (I) wherein Z is phenylene, m is zero and Y is oxygen, reacting a compound of the formula (XII) or chemical equivalent thereof with a compound of the formula (XIII):

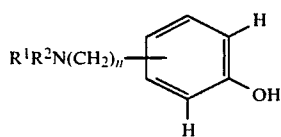

(XII)

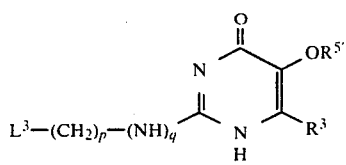

(XIII)

wherein $R^1$, $R^2$, n, p, q, $R^3$ and $R^{5'}$ are as hereinbefore defined and $L^3$ is a moiety displaceable by phenol or chemical equivalent thereof; or (g) for compounds of the formula (I) wherein R $R^1R^2N(CH_2)_n$—Z—, converting a compound of the formula (XIV):

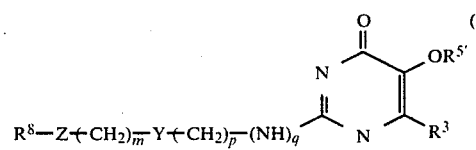

(XIV)

wherein Z, m, Y, p, q, $R^3$ and $R^{5'}$ are as hereinbefore defined and $R^8$ is a precursor of a group $R^1R^2N(CH_2)_n$—as hereinbefore defined; or (h) for compounds of the formula (I) wherein q is one, reducing a compound of the formula (XV):

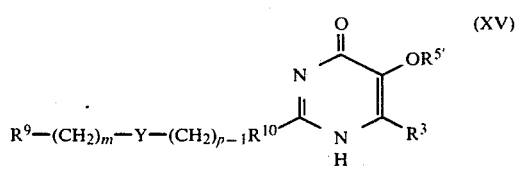

(XV)

wherein m, Y, p, $R^3$ and $R^{5'}$ are as hereinefore defined, $R^9$ is a group $R^o$ or $R^8$—Z—as hereinbefore defined and $R^{10}$ is a group —CH=N— or —CO—NH—;
and thereafter where necessary :

(i) reacting a compound wherein $R^6$ is furan-2-yl or thien-2-yl with a Mannich reagent to form a compound of the formula (I) wherein n is one;

(ii) converting a protected hydroxy group to hydroxy;

(iii) optionally forming a salt.

Suitably Q is nitroamino, $C_{1-6}$alkylthio, benzylthio, chloro or bromo. Of these methylthio is preferred.

The reaction between a compound of the formula (II) and a compound of formula (III) can be performed, at an elevated temperature, in the absence of solvent or in the presence of a substantially inert polar solvent. When Q is methylthio the reaction may be performed for example in the absence of solvent at 140°–170° C, or the reaction may be performed in a substantially inert solvent under reflux conditions, for example in a $C_{1-6}$alkanol, pyridine or anisole.

Examples of the moiety L include chloro, bromo, hydroxy, $C_{1-6}$alkoxy for example methoxy, $C_{1-6}$alkanoyloxy for example acetoxy, arylsulphonyloxy for example 4-methylbenzenesulphonyloxy, or $C_{1-6}$alkylsulphonyloxy for example methanesulphonyloxy.

Preferably L is hydroxy in which case the reaction between the compounds of the formulae (IV) and (V) is performed under acidic conditions. When L is chloro or bromo it is preferable to perform the reaction in the presence of a strong base for example sodium ethoxide in ethanol. When L is an arylsulphonyloxy or alkylsulphonyloxy group the reaction is preferably performed under mildly basic conditions for example in pyridine solution.

In the reaction of compounds of the formulae (IV) and (V), when carried out under basic conditions about one equivalent of base is used in order that a thiolate anion is preferentially formed on the $HS(CH_2)_q$—moiety. When performed under basic conditions the group $R^{5'}$ represents a protected group $R^4$.

Suitably in the reaction of compounds of the formulae (VI) and (VII) $L^l$ is chloro, bromo, arylsulphonyloxy for example 4-methylbenzenesulphonyloxy or $C_{1-6}$alkylsulphonyloxy for example methylsulphonyloxy. Such reactions are generally performed in the presence of a base for example triethylamine, an alkoxide or a hydroxide.

The compound of the formula (IX) is depicted as a ketone or aldehyde, dependent on whether $R^3$ is alkyl or hydrogen. This invention covers the reaction of chemical equivalents of such depicted compounds, as known in the art, for example protected or 'masked' aldehydes and ketones, for example an acetal.

When it is desired to form a compound of the formula (I) wherein $R^3$ is hydrogen, then for example a compound of the formula (VIII) may be reacted with a compound of the formula (IXA) and thereafter deprotecting if necessary:

(IXA)

wherein $R^7$ and $R^5$ are as hereinbefore defined and X is a displaceable group. For example X may be hydroxy (in which case the form depicted is tautomeric with formula (IX)) or a derivative thereof, so that for example X is protected hydroxy such as silyloxy, an acid residue RCO—O— (for example $C_{1-6}$alkanoyloxy), or an ether forming residue (for example $C_{1-6}$alkoxy such as methoxy or ethoxy). Additional examples for X include secondary and tertiary amino groups, for example di-$C_{1-6}$-alkylamino such as dimethylamino, cyclic amines such as piperidino, pyrrolidino and morpholino, anilino and 1-imidazolyl. Preferably X is $C_{1-6}$alkoxy and in particular ethoxy.

In compounds of the formulae (IX) and (IXA) the ester-forming group $R^7$ can be a $C_{1-4}$alkyl group and is preferably methyl or ethyl.

The reaction between the compounds of formulae (VIII) and (IX) or (IXA) is carried out in the presence of base. Examples of suitable bases include alkali metal hydroxides and $C_{1-4}$alkoxides, sodium hydride, and quaternary ammonium hydroxides, for example benzyltrimethylammonium hydroxide. Preferably the base is sodium ethoxide or sodium methoxide. The reaction can be carried out in the presence of a solvent the choice of which is not critical to the success of the process provided that it is substantially inert to the reagents and product. Preferably the solvent is a $C_{1-4}$alkanol, (for example, methanol, ethanol or propanol) or dimethylformamide. The reaction can be carried out at moderate temperatures, for example from room temperature to the reflux temperature of the solvent.

Suitably in the compounds of the formula (X), $L^2$ is chloro or bromo. The reaction of a compound of the formula (X) with a compound of the formula (XI) is generally performed under basic conditions, for example the anion of the compound of the formula (XI) may be generated, for example using sodium hydride in a suitable solvent.

In the reaction between the compounds of the formulae (XII) and (XIII) suitably $L^3$ is chloro or bromo. Suitably the reaction is performed under basic conditions, for example the anion of the compound of the formula (XII) may be generated, for example using sodium hydride. The reaction is performed in a suitable aprotic solvent for example dimethylformamide at a non-extreme temperature for example between 0° C and 100° C, suitably between ambient and 70° C.

In the compounds of the formulae (XIV) and (XV) in one suitable aspect $R^8$ is a group $R^1R^2N(CH_2)_xCO(CH_2)_y$—wherein $x+y=n-1$. Favourably x and y are both zero so that the group $R^1R^2NCO$— is a precursor to the group $R^1R^2$—. The conversion of such a group $R^1R^2N(CH_2)_xCO(CH_2)_y$—may be performed by reduction for example with a hydride for example lithium aluminium hydride.

In an alternative aspect $R^8$ is a group $CHO(CH_2)_{n-1}$—which may be converted to a group $R^1R^2N(CH_2)_n$—on reaction with an amine $R1R2NH$ under conditions of reductive amination. Furthermore in another suitable aspect $R^8$ may be a group $HO(CH_2)_n$—which may be converted directly to $R^1R^2N(CH_2)_n$—or indirectly thereto for example via a moiety such as $Br(CH_2)_n$—and thence to $R^1R^2)_n$—. Such transformations may be caried out in conventional manner.

The compounds of the formula (XV) may be carefully reduced to form compounds of the formula (I) wherein q is one, for example using lithium aluminium hydride in an ether solvent when $R^{10}$ is —CONH—; and for example using a borohydride in an alkanol, lithium aluminium hydride in an ether solvent, or catalytically hydrogenating when $R^{10}$ is —CH=N—.

Suitabel protected hydroxy groupls $OR^5$ and $OR^{5'}$ are those which may be converted to hydroxy by hydrolysis or by hydrogenolysis in conventional manner. These include optionally substituted benzyloxy groups referred to above. Suitably acid hydrolysis of a benzyloxy group to a hydroxy group may be employed.

Suitably functional groups on the group $R^4$ may be protected and deprotected in conventional manner.

For converting a compound wherein $R^6$ is furan-2-yl or thien-2-yl to a compound of the formula (I) wherein m is 1, suitable Mannich reagents include formaldehyde and an amine $R^1R^2NH$ or salt thereof. Such a reaction may be carried out by treatment of an amine salt with aqueous formaldehyde and a compound wherein $R^6$ is unsubstituted furan-2-yl or thien-2-yl, or by heating an amine salt with paraformaldehyde and a compound wherein $R^6$ is unsubstituted furan-2-yl or thien-2-yl, in a convenient solvent such as ethanol. Alternatively where $R^1$ and $R^2$ are both $C_{1-4}$alkyl, the Mannich reagent may be a di-($C_{1-4}$alkyl)methylene ammonium salt for example dimethylmethylene ammonium chloride or iodide, or may be a bis di-$C_{1-4}$alkylaminomethane, for example bis(dimethylamino)methane. Similarily, or concurrently, a group —$CH_2NR^aR^b$ may be introduced on to a furanyl- or thienyl- alkoxy group $R^4O$—.

Any group in the remainder of the molecule that is capable of reacting with a Mannich reagent may be optionally protected during the reaction, and may be subsequently deprotected in conventional manner. Thus any deprotection of the 5-pyrimidinone substituent is preferably performed after the Mannich reaction.

The formation of the group $R^1R^2N(CH_2)_n$—may be performed at any convenient stage of the synthetic procedures outlined herein or in the art. Such introduction may be direct or may involve two or more steps for example converting a hydroxyalkyl substituent to bromoalkyl and subsequently to $R^1R^2N(CH_2)_n$—.

Pharmaceutically acceptable acid addition salts of the compounds of the formula (I) may be prepared from the corresponding base of the compounds of the formula (I) in conventional manner. For example the base may be reacted with an acid in a $C_{1-4}$alkanol, or an ion-exchange resin may be used. The salts of the compounds of the formula (I) may be interconverted using ion-exchange resins. Non-pharmaceutically acceptable salts are therefore of use as they can be converted to pharmaceutically acceptable salts.

Suitable pharmaceutically acceptable acid addition salts of the compounds of the formula (I) include those formed with hydrochloric, hydrobromic, sulphuric, phosphoric, acetic, citric, maleic, lactic, ascorbic, fumaric, oxalic, methanesulphonic and ethanesulphonic acids.

The compounds of the formula (II), (IV), (VI), (VIII) and (X) may be prepared by the methods known to the art for example by methods described in U.S. Pat. Nos. 4,234,588, 4,227,000, 4,255,428, 4,385,058, U.S. Pat Nos. 4,496,567, 4,521,418 and 4,524,071.

The compound of the formula (III) wherein Q is $C_{1-6}$alkylthio or benzylthio may be prepared by the formula (XVI):

wherein $R^3$, $R^5$ and $R^7$ are as hereinbefore defined, $R^{11}$ $C_{1-6}$alkoxy; with thiourea and R is hydroxy or followed by alkylation or benzylation. The compounds of the formula (III) wherein Q is nitroamino may be prepared by the reaction of a compound of the formula (XVI) with nitroguanidine in conventional manner. Compounds of the formula (III) with other values of Q may be prepared in conventional manner.

Compounds of formula (V) wherein q is one may be prepared by the reaction of a corresponding compound of the formula (III) with an aminoalkylthiol or protected derivative thereof. Compounds of the formulae (XI), (VII) or (XIII) wherein q is one may be prepared by the reaction of a corresponding compound of the formula (III) with an aminoalkanol and if necessary subsequently converting a hydroxy group to a group $L^1$ or a group $L^3$.

The compounds of the formula (V) wherein q is zero may be prepared by the reaction of a compound of the formula (XVII):

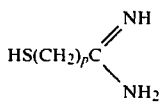 (XVII)

wherein p is as hereinbefore defined and the thiol moiety is suitably protected, with a compound of the formula (IX) or (IXA), under similar conditions to those described hereinbefore for the reaction with compounds of the formula (VIII). The compounds of the formula (XI), (VII) and (XIII) wherein q is zero may be prepared from conversion of the thiol group of compounds of the formulae (V) or may be prepared by the reaction of a formula (XVIII):

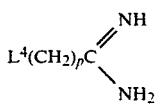 (XVIII)

wherein $L^4$ is hydroxy or a group $L^1$ or $L^3$ as hereinbefore defined and p is as hereinbefore defined, and $L^4$ is suitably protected if desired, with a compound of the formula (IX).

The compounds of the formulae (XVII) and (XVIII) may be prepared from the corresponding nitriles.

The compounds of the formula (XIV) may be prepared in a manner analogous to that described for the preparation of compounds of the formula (I), for example reacting a compound of the formula (III) with an analogue of the formula (II) wherein $R^6$ is replaced by $R^8$, provided that $R^8$ is suitably protected as necessary.

The compounds of the formula (XV) wherein $R^{10}$ is —CH=N may be prepared by the reaction of a compound of the formula (XIX) with a compound of the formula (XX):

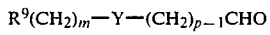

$$R^9(CH_2)_m\text{—}Y\text{—}(CH_2)_{p-1}CHO \quad (XIX)$$

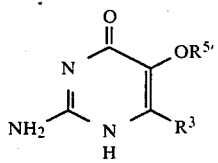 (XX)

wherein $R^9$, m, Y, p, $R^3$ and $R^{5'}$ are as hereinbefore defined, optionally in the presence of an acid catalyst. 25 The compounds of the formula (XV) wherein $R^{10}$ is —CONH— may be prepared by the reaction of a compound of the formula (XX) with an activated derivative of a compound of the formula (XXI):

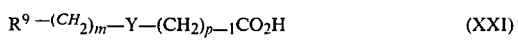

$$R^9\text{—}(CH_2)_m\text{—}Y\text{—}(CH_2)_{p-1}CO_2H \quad (XXI)$$

wherein $R^9$, m, Y and p are as hereinbefore defined. Suitable active derivatives are acyl halides, anhydrides and activated esters. The aldehydes of the formula (XIX) may be prepared for example by reacting a compound of the formula (XII) with a protected bromopropionaldehyde (for example protected as a cyclic acetal) and deprotecting. The acid of the formula (XXI) and derivatives thereof may be prepared in a similar manner for example by reacting a compound of the formula (XII) with a protected bromopropionic acid and if necessary deprotecting and/or converting to the desired activated acid derivative.

The following Examples serve to illustrate this invention.

EXAMPLE 1

2-[3-[3-(Piperidinomethyl)phenoxy]propyl]-5-benzyloxypyrimidin-4-one

To a stirred suspension of sodium (0.28 g) in toluene (15 ml) was added dropwise over 15 minutes a mixture of ethyl benzyloxyacetate (1.94 g) and ethyl formate (0.89 g). The mixture was stirred for 6 hours and allowed to stand overnight, giving the sodium salt of ethyl 3-oxo-2-benzyloxypropionate as a yellow solid. Toluene was evaporated under reduced pressure.

In another flask, to a stirred solution of sodium (0.28 g) in methanol (10 ml) was added 4-[3-(piperidinomethyl) phenoxy]butyronamidine hydrochloride (3.12 g) in methanol (15 ml). Sodium chloride precipitated, the mixture was stirred under reflux for 30 minutes, cooled and filtered through diatomaceous earth. The filtrate and the above formed sodium salt of the formyl ester were stirred under reflux for 26 hours. The mixture was cooled, evaporated under reduced pressure and water (25 ml) was added. The resultant oily residue was extracted into chloroform (containing a trace of isopropanol) (3×30 ml); the combined chloroform extracts were washed with water, dried (MgSO$_4$) and evaporated under reduced pressure. The residue was triturated under diethyl ether to give the title compound as a white solid (0.48 g). Further material (0.56 g) was obtained from chromatographic purification of the mother liquor. Recrystallisation from isopropanol methanol gave the title compound (0.87 g), m.p. 158°–159.5° C.

EXAMPLE 2

2-[3-[3-(Piperidinomethyl)phenoxy]propyl]-5-hydroxypyrimidin -4-one

2-[3-[3-(Piperidinomethyl)phenoxy]propyl]-5-benzyloxypyrimidin-4-one (0.68 g) was stirred under reduced pressure and taken to pH 8 with hours in 1N hydrochloric acid (20 ml). The mixture was concentrated under reduced pressure and taken to pH 8 with aqueous sodium bicarbonate. This mixture was extracted with n-butanol (3×20 ml); these extracts were combined, washed with water (2'5 ml), dried (MgSO$_4$) and evaporated under reduced pressure to give the title compound. This was dissolved in methanol containing ethanolic HCl, excess solvent was evaporated under reduced pressure and the residue crystallised from isopropanol-acetone to give 2-[3-[3-(piperidinomethyl)-phenoxy]propyl]-5-hydroxypyrimidin -4-one dihydrochloride (0.24 g), m.p. 192°–4° C.

EXAMPLE 3

2-[3-[3-(Piperidinomethyl)phenoxy]propyl]-5-methoxypyrimidin -4-one

The sodium salt of ethyl 3-oxo-2-methoxypropionate was obtained from ethyl methoxyacetate (1.18 g) and ethyl formate (0.89 g) by a method analogous to that of Example 1. This was stirred under reflux for 30 hours with the filtrate from the reaction of 4-[3-(piperidinomethyl)-phenoxy] butyronamidine hydrochloride (3.12 g) and sodium (0.28 g) (see Example 1).

The reaction mixture was cooled, evaporated under reduced pressure and water (25 ml) added. The solution was extracted with diethyl ether (3×20 ml), taken to pH 9 with glacial acetic acid and extracted into chloroform (3×25 ml). The combined chloroform washings were dried (MgSO4) and evaporated under reduced pressure. The residue was crystallised from diethyl ether to give the title compound (1.36 g), m.p. 124°–126.5° C (recrystallisation from isopropanol-ether).

EXAMPLE 4

2-[3-[3-(Piperidinomethyl)phenoxy]propyl]-5-ethoxy-pyrimidin-4-one

In a method analogous to Example 3 and on the same molar scale, ethyl ethoxyacetate (1.32 g), ethyl formate (0.89 g) and 4-[3-(piperidinomethyl)phenoxy]-butyronamidine hydrochloride (3.12 g) gave the title compound (0.97 g) as a white solid on crystallisation from isopropanol-ether, m.p. 104.5°–105.5° C.

EXAMPLE 5

2-[3-[3-(Piperidinomethyl)phenoxy]propylamino]-5-methoxypyrimidin-4-one (i) 2-Nitroamino-5-methoxypyrimidin-4-one To a stirred suspension of sodium (0.97 g) in toluene (50 ml) was added dropwise over 60 minutes a mixture of ethyl methoxyacetate (4.73 g) and ethyl formate (3.11 g). This was stirred for 6 hours and allowed to stand overnight to form, as a yellow solid, the sodium salt of ethyl 3-oxo-2-methoxypropionate. Toluene was evaporated under reduced pressure.

Nitroguanidine (4.16 g) in ethanol (50 ml) was added to the residue and the mixture was stirred under reflux for 7 hours, cooled, and evaporated under reduced pressure. Water (60 ml) was added to the residue, the resultant mixture was filtered and the filtrate washed with diethyl ether (3×40 ml). The aqueous solution was taken to pH 4 with glacial acetic acid to precipitate 2-nitroamino-5-methoxypyrimidin-4-one (2.28 g), m.p. 220°–5° (decomp) (recrystallisation from acetic acid-water).

(ii) 2-[3-[3-(Piperidinomethyl)phenoxy]propylamino]-5-methoxy -pyrimidin-4-one

3-[3-(Piperidinomethyl)phenoxy]propylamine (1.64 g) and 2-nitroamino-5-methoxypyrimidin-4-one (1.12 g) were stirred under reflux, for 40 hours, in ethanol (15 ml). The ethanol was replaced by pyridine (15 ml) and the solution stirred under reflux for a further 10 hours to complete the reaction. The reaction mixture was cooled and evaporated under reduced pressure to give a residue. This was partitioned between water (25 ml) and chloroform (25 ml), the aqueous layer being further extracted with chloroform (2×25 ml). The combined chloroform extracts were dried (MgSO4), evaporated under reduced pressure and subjected to medium pressure chromatography using chloroform: methanol (95 : 5) to give the title compound. The fractions containing the title compound were dissolved in isopropanol and treated with maleic acid (0.6 g) in isopropanol to give 2-[3-[3-(piperidinomethyl)phenoxy]propylamino]-5-methoxypyrimidin-4-one maleate (0.96 g), m.p. 148°–149.5° C (recrystallisation from ethanol).

EXAMPLE 6

2-[2-[3-(Piperidinomethyl)phenoxy]ethylamino]-5-methoxy -pyrimidin-4-one

2-[3-(Piperidinomethyl)phenoxy]ethylamine * (1.38 g) and 2-nitroamino-5-methoxypyrimidin-4-one(1.00 g) were stirred under reflux, for 19 hours, in pyridine (15 ml). The reaction mixture was worked-up in a manner analogous to that of Example 5 to give the title compound which was converted to 2-[2-[3-(piperidinomethyl)phenoxy]-ethylamino]-5-methoxypyrimidin-4-one maleate.

Belgian Patent 895.076

EXAMPLE 7

2-[3-[3-(Piperidinomethyl)phenoxy]propylamino]-5-ethoxy -pyrimidin-4-one (i) 2-Nitroamino-5-ethoxypyrimidin-4-one To a stirred suspension of sodium (0.97 g) in toluene (50 ml) was added dropwise over 50 minutes, a mixture of ethyl ethoxyacetate (5.29 g) and ethyl formate (3.19 g). This mixture was stirred for 6 hours and allowed to stand overnight. Toluene was evaporated under reduced pressure and nitroguanidine (4.16 g) in ethanol (60 ml) added to the residue. The resultant mixture was stirred under reflux conditions for 7 hours and allowed to stand overnight. Ethanol was evaporated under reduced pressure, water (50 ml) was added and the mixture was filtered. The filtrate was washed with diethyl ether (3×40 ml), taken to pH 4 with glacial acetic acid, cooled and 2-nitroamino-5-ethoxypyrimidin-4-one was filtered off, washed and dried to give a light-buff solid (3.27 g), m.p. 189°–192° C.

(ii) 2-[3-[3-(Piperidinomethyl)phenoxy]propylamino]-5ethoxy-pyrimidin-4-one

3-[3-(Piperidinomethyl)phenoxy]propylamine (1.64 g), 2-nitroamino-5-ethoxypyrimidin-4-one (1.2 g) and pyridine (15 ml) were stirred under reflux conditions for 18 hours. Pyridine was evaporated under reduced pressure and water (25 ml) and chloroform (25 ml) added. The mixture was shaken, the chloroform layer extracted; the aqueous layer was further extracted with chloroform (2×25 ml), and the combined chloroform extracts were washed with water, dried (MgS04) and evaporated under reduced pressure. The resultant residue was subjected to column chromatography on silica gel using chloroform: methanol (95:5) as eluant. The desired fractions were evaporated to give the title product as a residue. This residue was washed with diethyl ether and dissolved in isopropanol. This solution was treated with maleic acid (0.77 g) in isopropanol to give a solid maleate salt which on crystallisation from ethanol gave 2-[3-[3-(piperidinomethyl)phenoxy]-propylamino ]-5-ethoxypyrimidin-4-one dimaleate (1.11 g), m.p. 68°–71° C.

EXAMPLE 8

2-[3-[3-(Pyrrolidinomethyl)phenoxy]propyl]-5-methoxypyrimidin -4-one (i) 4-[3-(Pyrrolidinomethyl)phenoxy]butyronitrile 3-(Pyrrolidinomethyl)phenol (10 g) was dissolved in DMF (50 ml). The solution was cooled in ice and sodium hydride (2.98 g) added over 45 minutes. After stirring for a further 60 minutes 4-bromobutyronitrile (6.2 ml) was added dropwise. The mixture was then stirred at room temperature for a further 40 hours. Water was added (150 ml) and the pH of the solution adjusted to about 5 with glacial acetic acid. The solution was extracted with ether (3×100 ml). The aqueous layer was adjusted to pH 10 with K₂CO₃ and re-extracted with chloroform (3×100 ml). The chloroform extracts were washed with water, dried (MgSO₄) and evaporated to give a light brown oil (33.49 g). To remove residual DMF this oil was dissolved in ethyl acetate and the solution extracted (×6) with water. The ethyl acetate solution was finally dried (MgSO₄) and evaporated to give the product as a light brown oil (11.16 g).

(ii) 4-[3-(Pyrrolidinomethyl)phenoxy]butyronamidine hydrochloride

4-[3-(Pyrrolidinomethyl)phenoxy]butyronitrile (10 g) was dissolved in a mixture of dry methanol (60 ml) and chloroform (120 ml) under nitrogen and the solution cooled to 3° C. HCl gas was passed through the solution for 2 hours whilst keeping the temperature at about 0° C for a further ½ hour. The reaction mixture was then carefully poured into a solution of K₂CO₃ (50 g) in ice-water (350 ml). The chloroform layer was collected and the aqueous layer further extracted with chloroform (3×100 ml). The combined chloroform solutions were dried (MgSO₄) and evaporated to give methyl 4-[3-(pyrrolidinomethyl)phenoxybutyrimidate as a light brown oil (10.27 g). This imidate (10.27 g) and ammonium chloride (2.0 g) were stirred at room temperature in ethanol (80 ml) for 20 hours. The solution was evaporated to dryness, the residue dissolved in acetonitrile and a trace of ethanol and cooled to give pale-buff crystals of the amidine hydrochloride, 6.56 g; m.p. 147°–148.5° C.

(iii) 2-[3-[3-(Pyrrolidinomethyl)phenoxy]propyl]-5-methoxypyrimidin-4-one

Sodium (0.28 g) was added in small pieces to toluene (15 ml). A mixture of ethyl methoxyacetate (1.18 g) and ethyl formate (0.89 g) was added dropwise and the mixture stirred for 24 hours. Sodium gradually disappeared and was replaced by the sodium salt of ethyl 3-oxo-2-methoxypropionate, as a solid. Toluene was evaporated at reduced pressure. Sodium (0.28 g) was dissolved in methanol (10 ml) and a solution of the amidine hydrochloride (prepared in ii) above) (2.98 g) in methanol (15 ml) was added. The mixture was stirred under reflux for ½ hour, cooled and filtered and the filtrate added to the crude sodio-formyl ester prepared above. The mixture was stirred under reflux for 22 hours and then cooled. The methanol was evaporated off, the residue dissolved in water (about 25 ml) and the aqueous solution extracted with ether (3×20 ml) and then adjusted to pH9 (from pH about 12) with glacial acetic acid. The solution was re-extracted with chloroform (6×20 ml) and the combined chloroform extracts were dried (MgSO₄) and evaporated to dryness. The oily residue was triturated with ether to give a light-buff solid which was crystallised twice from isopropanol-ether to give the title compound as a light-buff, crystalline solid, 0.79 g; m.p. 92°–95° C.

EXAMPLE 9

A pharmaceutical composition for oral administration is prepared containing:

|   |   | % by weight |
|---|---|---|
| A | 2-[3-(3-(piperidinomethyl)phenoxy)-propyl]-5-benzyloxypyrimidin-4-one dihydrochloride | 55 |
|   | Dibasic calcium phosphate dihydrate | 20 |
|   | Approved colouring agent | 0.5 |
|   | Polyvinylpyrrolidone | 4.0 |
| B | Microcrystalline Cellulose | 8.0 |
|   | Maize Starch | 8.0 |
|   | Sodium glycollate | 4.0 |
|   | Magnesium Stearate | 0.5 | by mixing together the ingredients A (substituting lactose or microcrystalline cellose for dibasic calcium phosphate dihydrate if desired), adding a concentrated solution of polyvinylpyrrolidone and granulating, drying and screening the dried granules; adding the ingredients B to the dried granules and compressing the mixture into tablets containing 100 mg, 150 mg or 200 mg of the free base.

Other compounds of the invention, for example those specifically described in Examples 2 to 8 can be formulated into pharmaceutical compositions by a similar procedure.

The compounds of this invention, where tested, show no overt signs of toxicity at doses which are a pertinent multiple of the therapeutic dose.

What is claimed is:

1. A compound of the formula (I):

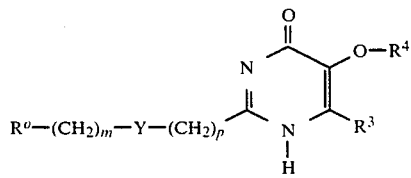

or a pharmaceutically acceptable salt thereof, wherein:
R⁰ is 2-guanidinothiazol-4-yl or a group R¹R²N(CH₂)ₙ—z—
wherein:
R¹ and R² are independently hydrogen, C₁₋₆alkyl, phenyl(C₁₋₆)alkyl, furanyl(C₁₋₆)alkyl, thienyl(C₁₋₆)alkyl, C₃₋₁₀cycloalkyl, hydroxy(C₂₋₆)alkyl, or halo (C₂₋₆)alkyl (wherein said hydroxy and halo groups are not substituted on the carbon atom adjacent to the nitrogen atom); or
R¹ and R² together represent —(CH₂)ᵣ—wherein r is 4 to 7, to form together with the nitrogen atom to which they are attached a 5–8 membered saturated ring;
n is an integer from 1 to 6;
z is 2,5-thienyl, 2,4-pyridyl wherein the R¹R²N(CH₂)ₙ group is in the 4-position, 2,4-thiazolyl wherein the R¹R²N(CH²)n group is in the 2-position, or 1,3- or 1,4-phenylene;
m is one; or if Z is pyridyl or phenylene m may also be zero;
Y is oxygen, sulphur or methylene; or if Z is furanyl, thienyl or thiazolyl Y may also be a bond;
p is two, three or four;
R³ is hydrogen or C₁₋₆alkyl; and
R⁴ is hydrogen of C₁₋₆alkyl.

2. A compound according to claim 1 wherein R³ is hydrogen.

3. A compound according to claim 1 wherein $R^4$ is hydrogen or methyl.

4. A compound according to any one of claims 1 to 2 wherein $R^1R^2N(CH_2)_n$—z— is 3-piperidinomethylphenyl.

5. A compound according to claim 1 which is:
2-[3-(3-(piperidinomethyl)phenoxy)propyl]-5-hydroxypyrimidin -4-one or a pharmaceutically acceptable salt thereof.

6. A compound according to claim 1 which is:
2-[3-(3-(piperidinomethyl)phenoxy)propyl]-5-methoxypyrimidin -4-one or a pharmaceutically acceptable salt thereof.

7. A compound according to claim 1 which is:
2-[3-(3-(piperidinomethyl)phenoxy)propyl]-5-ethoxypyrimidin -4-one or a pharmaceutically acceptable salt thereof.

8. A compound according to claim 1 which is:
2-[3-[3-(pyrrolidinomethyl)phenoxy]propyl]-5-methoxypyrimidin -4-one or a pharmaceutically acceptable salt thereof.

9. A pharmaceutical composition having histamine $H_2$-antagonist activity which comprises an effective amount of a compound according to claim 1 and a pharmaceutically acceptable carrier.

10. A method of blocking histamine $H_2$-receptors which comprises administering to an animal an effective amount to block said receptors of a compound of claim 1.

* * * * *

UNITED STATES PATENT AND TRADEMARK OFFICE
CERTIFICATE OF CORRECTION

PATENT NO. : 4,694,008

DATED : September 15, 1987

INVENTOR(S) : Thomas H. Brown and Graham J. Durant

It is certified that error appears in the above-identified patent and that said Letters Patent is hereby corrected as shown below:

Column 2, line 55: replace "2-guanidinothiazol4-methylthio" with -- 2-guanidinothiazol-4-ylmethylthio -- .

Column 3, line 31: replace "-(1,3-benzodioxolyl) with -- 5-(1,3-benzodioxolyl) -- .

Column 5, line 43: replace "(a) ror compounds of the formula (I) and salts thereof" with -- for compound of the formula (I) wherein q is -- .

Column 6, line 65: replace "L" with -- $L^2$ -- .

Column 7, line 20: replace "R" with -- $R^0$ is -- .

Column 8, line 48: delete numeral "30" at end of line.

Column 9, line 27: replace "$R^1R^2$-" with -- $R^1R^2NCH_2$- -- .

Column 9, line 38: replace "$R^1R^2)_n$-" with -- $R^1R^2N(CH_2)_n$- -- .

Column 9, line 48: replace "Suitabel" with -- Suitable -- .

Column 10, lines 49-50: replace "$R^{11}$ $C_{1-6}$alkoxy; with thiourea and R is hydroxy or" with -- and $R^{11}$ is hydroxy or $C_{1-6}$alkoxy; with thiourea -- .

Column 12, lines 43-44: replace "reduced pressure and taken to pH 8 with" with -- reflux for 24 -- .

Column 12, line 49: replace "(2'5 ml)" with -- (2x5 ml) -- .

UNITED STATES PATENT AND TRADEMARK OFFICE
CERTIFICATE OF CORRECTION

PATENT NO. : 4,694,008

DATED : September 15, 1987

INVENTOR(S) : Thomas H. Brown and Graham J. Durant

It is certified that error appears in the above—identified patent and that said Letters Patent is hereby corrected as shown below:

Claim 1, line 56: insert -- 2,5-furanyl -- before "2,5-thienyl".

Claim 1, line 66: replace "of" with -- or -- .

Claim 4: replace "claims 1 to 2" with -- claims 1 to 3 -- .

Signed and Sealed this

Seventeenth Day of May, 1988

Attest:

DONALD J. QUIGG

Attesting Officer

Commissioner of Patents and Trademarks